United States Patent [19]

Nickell

[11] Patent Number: 5,550,384
[45] Date of Patent: Aug. 27, 1996

[54] METHOD AND APPARATUS OF AUTOMATICALLY SCANNING FOR DENSITY DEFECTS IN CARPETS

[75] Inventor: Larry C. Nickell, Lewisburg, W. Va.

[73] Assignee: Appalachian Electronic Instruments, Inc., Ronceverte, W. Va.

[21] Appl. No.: 420,378

[22] Filed: Apr. 11, 1995

[51] Int. Cl.$^6$ .................................................. G01N 21/86
[52] U.S. Cl. .............................. 250/559.45; 250/559.46; 356/429
[58] Field of Search .......................... 250/559.12, 559.13, 250/559.15, 559.20, 559.21, 559.22, 559.27, 559.45, 559.46, 559.48; 356/236, 237, 429–431; 66/194; 139/391

[56] References Cited

U.S. PATENT DOCUMENTS

| | | | |
|---|---|---|---|
| 3,188,478 | 6/1965 | Binks | 250/559.48 |
| 3,589,816 | 6/1971 | Sugaya | 250/559.46 |
| 3,835,332 | 9/1974 | Bridges | 250/559.45 |
| 3,859,538 | 1/1975 | Mannonen | 250/559.46 |
| 3,877,821 | 4/1975 | Price et al. | 250/559.46 |
| 4,591,726 | 5/1986 | Schenk | 250/559.48 |

*Primary Examiner*—Stephone Allen
*Attorney, Agent, or Firm*—Popham, Haik, Schnobrich & Kaufman, Ltd.

[57] ABSTRACT

An apparatus and method for scanning a carpet is used for detecting tuft defects in the carpet during manufacture. The apparatus or system incorporates a light source for providing light along a width of the carpet; a scanning array for detecting light from the light source passing through the carpet; and control circuit means for controlling the sensor array to scan the carpet and for receiving the output signals from the first and second sensor cells detecting tuft defects in the carpet based on the light passing through the carpet. The scanning array has at least one pair of first and second sensor cells, and is positioned opposite the light source with the carpet passing transversely therebetween. Each of the first and second sensor cells includes first and second sets of sensor elements, and an output node between the first and second sets of sensor elements. The output node outputs a signal detecting tuft defects in the carpet based on an amount of light passing through the carpet. The first set of sensor elements of the second sensor cell is positioned adjacent the first set of the first sensor cell, the second set of the first sensor cell is positioned adjacent the first set of the second sensor cell, and the second set of the second sensor cell is positioned adjacent the second set of the first sensor cell.

22 Claims, 8 Drawing Sheets

METHOD AND APPARATUS OF AUTOMATICALLY SCANNING FOR DENSITY DEFECTS IN CARPETS

BACKGROUND OF THE INVENTION

1. Field of the Invention

The present invention relates to a method and apparatus for automatically scanning for defects in the density of a carpet during the manufacture of the carpet. More specifically, the invention relates to a method and apparatus for scanning a carpet for defects in the density of the tufts along the width of a carpet as it is being conveyed during its manufacture.

2. Related Art

In the manufacture of carpets, machines such as the Cobble Model Pantera are used to mass produce them. Such machines are designed to produce carpets with tufts that vary in density, pattern and color. In the course of producing the carpets, the machines may malfunction resulting in defects such as too much yarn being woven into the carpet, too little yarn being woven in, no yarn being woven into the carpet, holes, missed stitches, or low tuft lines. If the occurrence of defects are not carefully monitored, such defects may cause large amounts of material and machine hours to be wasted.

Consequently, quality control measures have been instituted by the manufacturers of carpets and other similar materials. However, such quality control measures are typically limited to the use of human operators observing the operation and output of the machines. When the operator sees a defect occurring, he/she stops the machine. The use of human operators has its limitations. Observing the output of carpet from a machine can become extremely tedious. Therefore, there is no guarantee that a person will be able to keep their full attention on the carpet during its entire production time. Also, due to the number of variations possible in the density, pattern and color of carpets, defects in some carpets may be more difficult than in others for the human eye to detect. Further, how well an operator is able to spot defects will depend on many variables including the individual operator's physical abilities (i.e., eyesight), the available lighting, the size of the carpet being observed, and the operator's physical location relative to the carpet. In general, too many variables exist in this form of quality control that a consistent and uniform level of monitoring the production of carpets cannot be assured.

One type of system for monitoring the operation of the machines currently known is the use of a photoelectric detector and a light beam source that detect when yarn used to make the tuff of a carpet falls out of the machine. This system is in no way capable of detecting any of the types of defects that the present invention is directed to monitoring.

All in all, there exists no system or device in industry designed to measure the density of a carpet in order to determine if any defects exist in the manufacture of the carpet. Instead, as shown above, the practices of the industry are limited to very rudimentary techniques that are either too inherently inconsistent or too limited in scope in order to embody a meaningful form of defect detection and monitoring.

SUMMARY OF THE INVENTION

In view of the limitations in the industry to date and the current state of the prior art, one main object of the present invention is to provide a method and apparatus for automatically scanning a carpet during manufacture for defects.

Another object of the present invention is to provide an apparatus for automatically scanning a carpet or other material for defects in order to control the manufacture of the carpet or other material.

A further object of the present invention is to provide an apparatus for automatically scanning a carpet or other material being scanned in conjunction with the manufacture of the carpet that is capable of distinguishing between local defects and wide scale defects resulting from machine malfunctions.

An even further object of the present invention is to provide a microprocessor- or computer-controlled system for automatically scanning a carpet or other material in conjunction with the manufacture of the carpet that monitors for both local defects in the carpet or other material and wide scale defects resulting from machine malfunctions.

Similarly, another object of the present invention is to provide a method based on a microprocessor- or computer-controlled system for automatically scanning a carpet or other material in conjunction with the manufacture of the carpet that monitors for both local defects in the carpet or other material and wide scale defects resulting from machine malfunctions.

Yet another object of the present invention is to provide an automated system for scanning a carpet or other material during the manufacture of the carpet or other material that uses a relatively simple structure and operation for scanning the carpet.

Also similarly, another object of the present invention is to provide a method for automatically scanning a carpet or other material during manufacture that monitors for both local defects in the carpet or other material and wide scale defects resulting from machine malfunctions using a relatively simple structure and operation.

In at least a first embodiment, the invention is directed to a system for automatically scanning a carpet for tuft defects that incorporates a light source for providing light along a width of the carpet; a scanning array for detecting light from the light source passing through the carpet; and control circuit means for controlling the sensor array to scan the carpet and for receiving the output signals from the first and second sensor cells detecting tuft defects in the carpet based on the light passing through the carpet. The scanning array has at least one pair of first and second sensor cells, and is positioned opposite the light source with the carpet passing transversely therebetween. Each of the first and second sensor cells includes first and second sets of sensor elements, and an output node between the first and second sets of sensor elements. The output node outputs a signal detecting tuft defects in the carpet based on an amount of light passing through the carpet. The first set of sensor elements of the second sensor cell is positioned adjacent the first set of the first sensor cell, the second set of the first sensor cell is positioned adjacent the first set of the second sensor cell, and the second set of the second sensor cell is positioned adjacent the second set of the first sensor cell.

The method of the invention for scanning a carpet for tuft defects during manufacture is generally implemented in a system where a scanning array is provided opposite and parallel a light source with the carpet passing transversely therebetween, and the scanning array is provided with a plurality of pairs of first and second sensor cells for detecting light passing through the carpet. The plurality of first and second sensor cell pairs are positioned adjacent each other longitudinally in the scanning array. Each of the first and second sensor cells are provided with a first and second set of sensor elements, and each of the first and second sensor cells outputs an output signal indicating an electrical balance between the first and second sets of sensor cells. Further, the first set of sensor elements from the second sensor cell are positioned adjacent the first set from the first sensor cell, the second set from the first sensor cell being positioned adjacent the first set from the second sensor cell, and the second set from the second sensor cell positioned adjacent the second set from the first sensor cell. The method includes the steps of scanning a stitch of the carpet along an entire width of the carpet with the scanning array; detecting output signals from each of the plurality of first and second sensor cells based on an amount of light detected by each of the plurality of first and second sensor cells; and determining whether the output signals indicate detection of tuft defects in the carpet based on the amount of light detected by the plurality of first and second sensor cells.

BRIEF DESCRIPTION OF THE DRAWINGS

The invention is better understood by reading the following Detailed Description of the Preferred Embodiments with reference to the accompanying drawing figures, in which like reference numerals refer to like elements throughout, and in which.

DETAILED DESCRIPTION OF THE PREFERRED EMBODIMENTS

Figure 1:
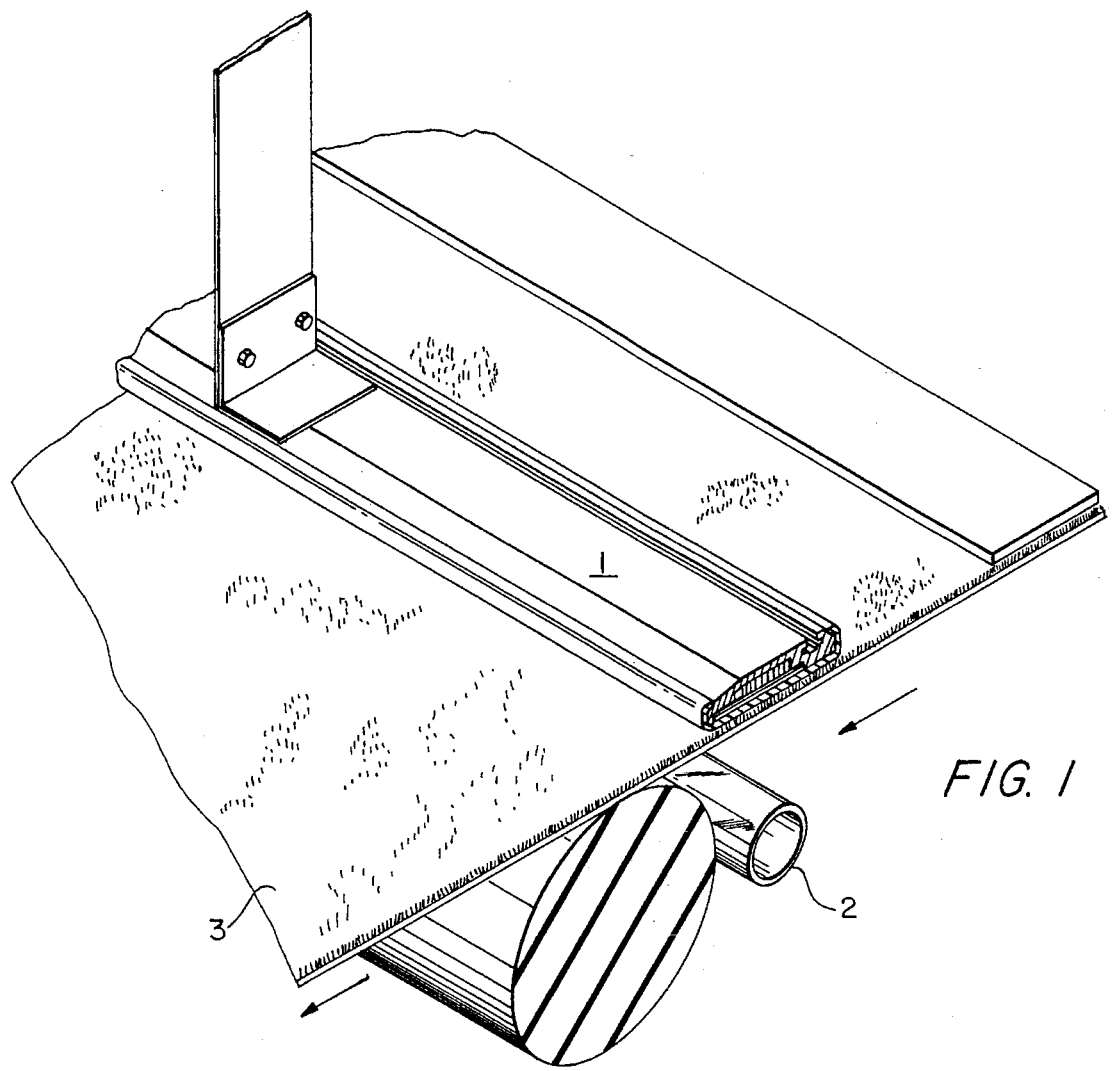
FIG. 1 illustrates an overall perspective view of the invention in one application thereof.

In describing preferred embodiments of the present invention illustrated in the drawings, specific terminology is employed for the sake of clarity. However, the invention is not intended to be limited to the specific terminology so selected, and it is to be understood that each specific element includes all technical equivalents which operate in a similar manner to accomplish a similar purpose.

In a first embodiment of the present invention, the apparatus of the invention as illustrated in FIG. 1 generally incorporates a sensor assembly 1 positioned opposite to and facing a high frequency fluorescent lamp 2. The carpet 3 or other material being scanned passes between the scanner assembly and the fluorescent lamp 2 in a direction transverse to the length of the sensor assembly 1 and lamp 2.

Figure 2:
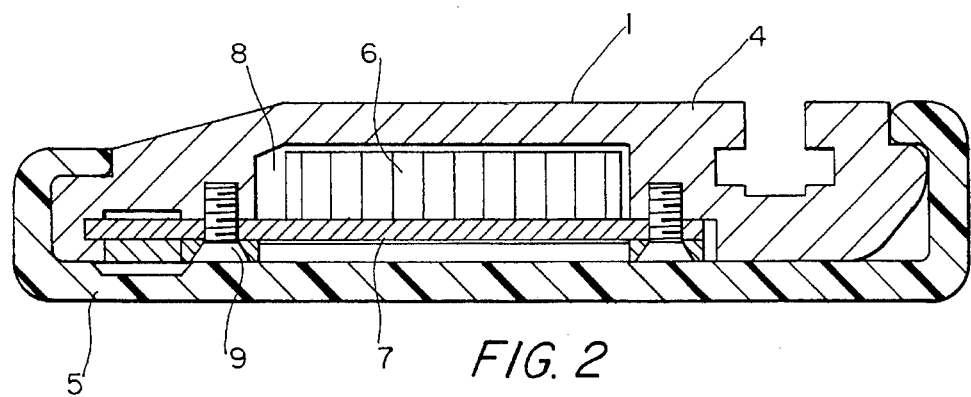
FIG. 2 illustrates sectional view of the sensor assembly from the apparatus of the invention.

The sensor assembly 1 as shown in FIG. 2 consists of a mounting frame 4, sensor cells 6 mounted on a plurality of sensor circuit boards 7, and a protective cover 5. The sensor circuit boards 7 are mounted in an inner cavity 8 of the mounting frame 4 with the sensor cells 6 facing outward. The protective cover 5 is positioned on the mounting frame 4 with the sensor circuit boards 7 sandwiched between them.

Figure 3:
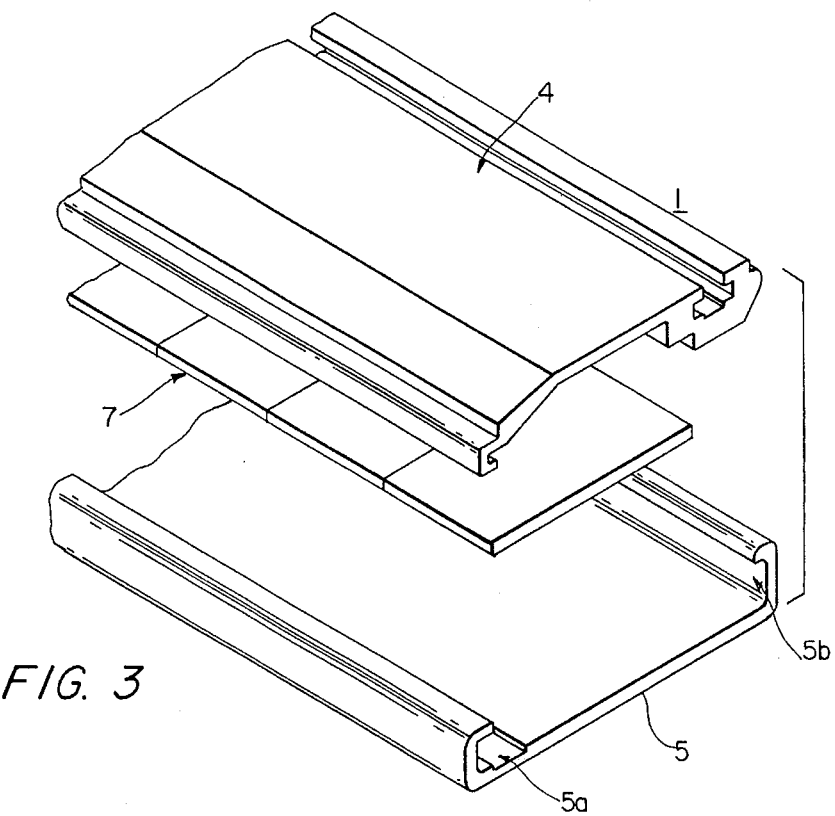
FIG. 3 illustrates an exploded view of the sensor assembly from the apparatus of the invention.

As illustrated in FIGS. 1 and 3, the mounting frame 4 is an elongated structure designed to extend the width of the carpet 3 or other material being scanned. In this first embodiment of the invention, the mounting frame 4 is formed as one-piece using extruded aluminum. The mounting frame 4 is further formed with an inner cavity 8 to accommodate a plurality of sensor circuit boards 7 along its entire length, along with the appropriate mounting features to mount the sensor circuit boards therein and to securely attach the protective cover 5 to the mounting frame 4. For example, the sensor circuit boards 7 may be mounted to the mounting frame 4 using screws 9 coupled to threaded holes in the mounting frame 4. The protective cover 5 may be formed with channels 5a, 5b on both of its longitudinal edges that engage with the corresponding longitudinal edges of the mounting frame 4.

Like the mounting frame 4, the protective cover 5 as shown in FIGS. 1 and 3 is also an elongated structure extending the length of the mounting frame 4. The protective cover 5 is also designed to be optically diffusive at least between the sensor cells 6 facing the fluorescent lamp 2 and the carpet 3 or other material being scanned. In this first embodiment, the protective cover 5 is formed as one piece from UHMW polyethylene plastic. The protective cover 5 may be used not only to diffuse the light from the lamp 2 and protect the sensor cells 6, but also as shown in FIG. 1 to press on the carpet 3 as it passes by the sensor assembly 1.

Figure 4:
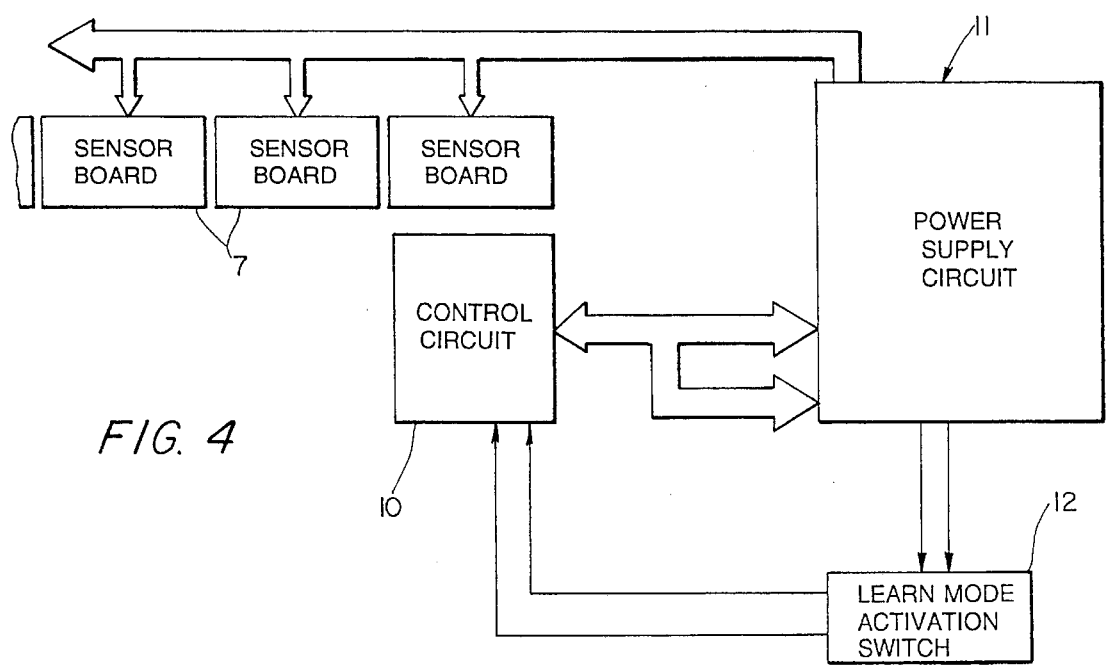
FIG. 4 illustrates a general circuit block diagram of the entire system of the invention.

In general, the system of the present invention as shown in FIG. 4 incorporates the plurality of sensor circuit boards 7, a control circuit 10, an intermediate power supply circuit 11 and a LEARN mode activation switch 12.

Figure 5:
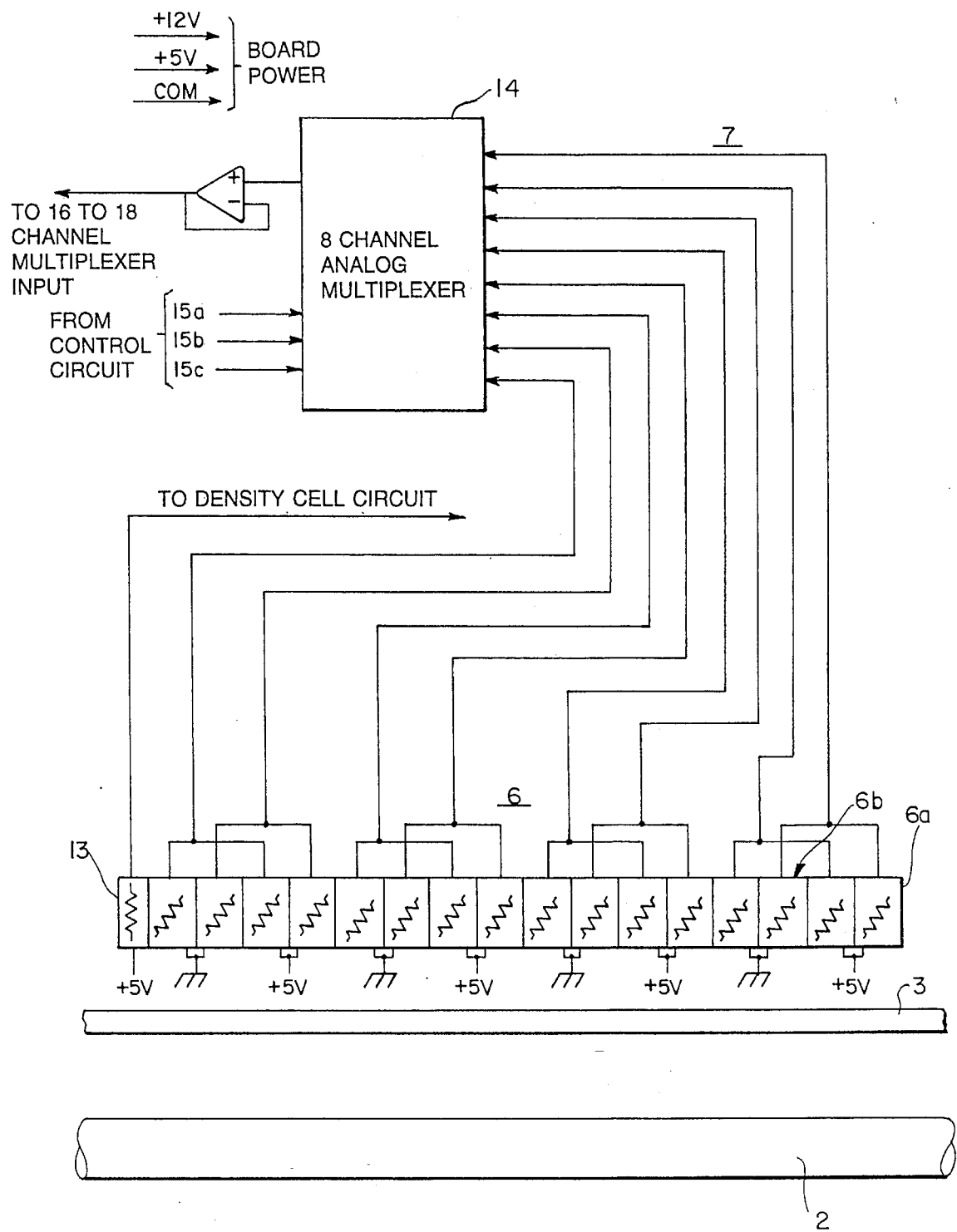
FIG. 5 illustrates a circuit block diagram of the sensor circuit of the apparatus of the invention.
Figure 6:
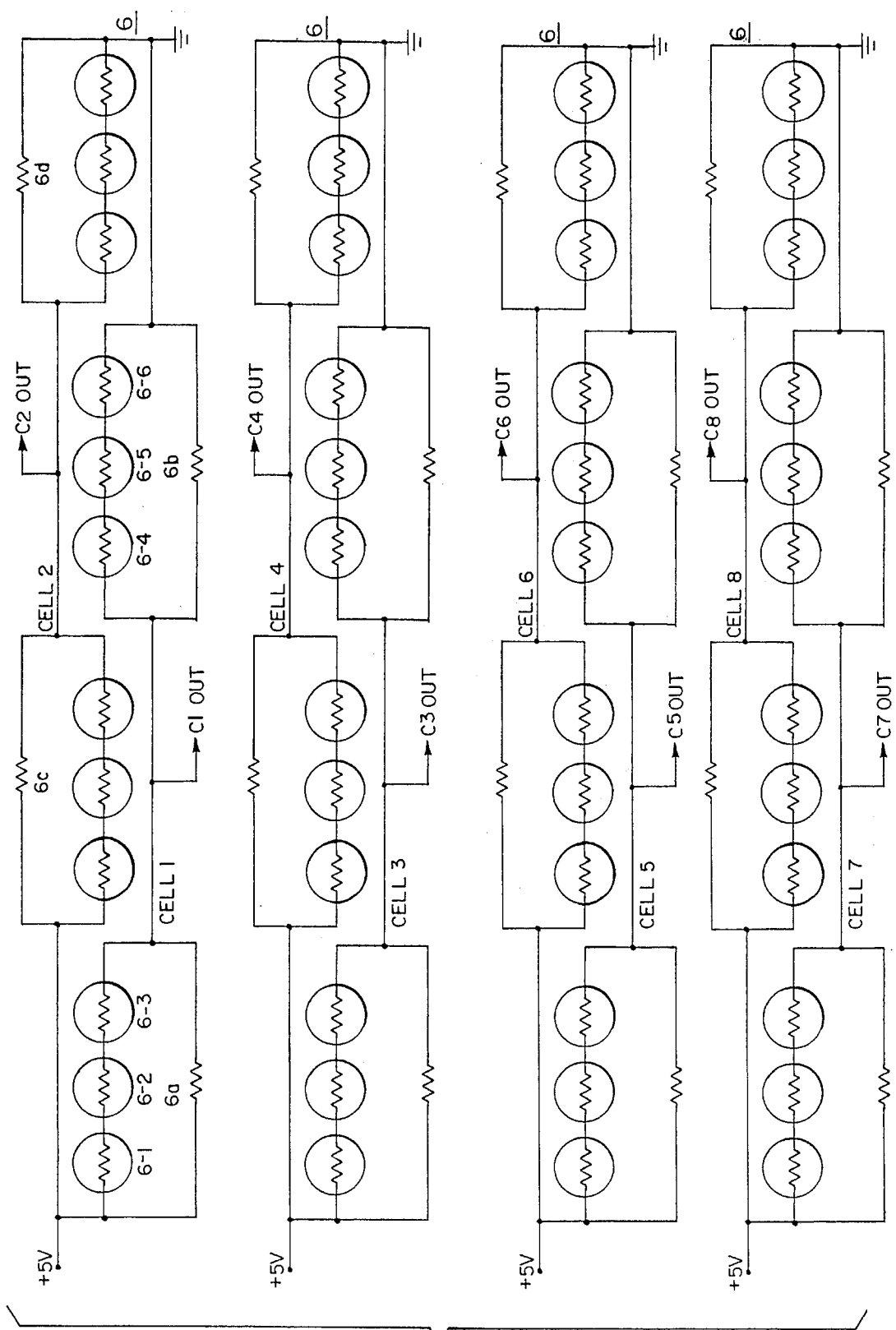
FIG. 6 illustrates a general circuit diagram of the sensor cells from the apparatus of the invention.

As shown in FIG. 5, each of the sensor circuit boards 7 in the sensor assembly 1 incorporates a plurality of sensor cells 6 and a multiplexer circuit device 14 for multiplexing the signals from the sensor cells 6. Each of the plurality of sensor cells 6 is connected to an input 14a–14h of the multiplexer circuit device 14. In FIG. 6, each sensor cell 6 consists of a plurality of sensor elements 6-1 through 6-6 that are grouped into two matching sets 6a–6b or 6c–6d of sensor elements 6-1 to 6-6. In addition, each sensor circuit board 7 may also include a density sensor cell 13 having a single sensor element. In this first embodiment, all the sensor elements 6-1 to 6-6 in each sensor cell are physically arranged side-by-side. Correspondingly, all the sensor cells 6 in each sensor circuit board 7 are arranged side-by-side, and all the sensor circuit boards 7 in the sensor assembly 1 are arranged side-by-side, whereby all the sensor elements together side-by-side extend along the entire length of the sensor assembly 1.

Functionally, the sensor cells 6 are used for detecting light emitted by the fluorescent lamp 2 and passing through the carpet 3 or other material being scanned. Specifically, the plurality of sensor cells 6 are used to detect local changes or defects in the density of the carpet 3 based on the amount of light that passes through the carpet 3. The density sensor cell 13 is used to detect wide scale changes in the carpet density.

In this first embodiment, as shown in FIG. 6, eight sensor cells 6 are each composed of six sensor elements 6-1 to 6-6 arranged in series between the power source (+5 volts) and GND; the six sensor elements 6-1 to 6-6 are set up as matched sets 6a–6b or 6c–6d of three sensor elements each. The output terminals of Cells 1–8 (C1OUT to C8OUT) are located between each cell's two sets 6a–6b or 6c–6d of sensor elements. For example, in Cell 1, the two sets of sensor elements are 6a, 6b and the output terminal is C1OUT. In Cell 2, the two sets of sensor elements are 6c, 6d and the output terminal of Cell 2 is C2OUT. The sensor elements 6-1 to 6-6 are in this case light sensitive resistors. The density sensor cell 13 uses a single light sensitive resistor.

Each light sensitive resistor has a 0.375 inch active area. In conjunction with the optically diffusive effect of the protective cover 5, the active area allows light passing through the carpet 3 to the sensor element to be integrated in a manner similar to the human eye. In particular, some photodetecting devices are sensitive to the frequencies and other spectral characteristics at which light from some types of fluorescent lamp 2 is generated. Consequently, detecting light at such frequencies or with such spectral characteristics results in output signals from the photodetecting devices that are filled with noise and variations. Such noise is equivalent to lamp "flicker" that is often detected by human eyes. In order to generate signals that would be usable by the control circuit 15, filtering and other processing circuitry would be needed to "clean up" the signals. However, to avoid incorporating overhead hardware and software to process noisy signals, one way used in the invention is the incorporation of light sensitive resistors and an optically diffusive protective cover 5 in its sensor assembly 1. The combination of the protective cover 5 and the light sensitive resistors is relatively insensitive to the noise and variations caused by fluorescent lamps. The net effect of the combination is a spectral response similar to the human eye. In addition, the invention in this first embodiment uses a high frequency lamp with a solid state bidlast and an operating frequency of 20,000 Hz. As a result, the control circuit 15 receives signals that are relatively clean and indicative of the light received by the light sensitive resistors.

The multiplexer circuit device 14 of FIG. 5 in this embodiment is a 74HC4051 8-channel analog multiplexer/demultiplexer whose input terminals 14a–14h are connected to the output terminals of eight sensor cells 6. The output terminal 14i of the multiplexer circuit device 14 is connected to the control circuit 15. Similarly, the output terminals of the multiplexer circuit devices from other sensor circuit boards 7 are connected to the control circuit 14.

In the arrangement of the sensor cells 6 of FIG. 6, each of the sensor cells 6 is paired with a second sensor cell (i.e., Cell 1 paired with Cell 2, Cell 3 paired with Cell 4, Cell 5 paired with Cell 6, Cell 7 paired with Cell 8). Each cell 6 is split into the two matching sets 6a, 6b of sensor elements 6-1 to 6-6 which will be referred to as first and second sets 6a, 6b or 6c, 6d. In the physical arrangement of each pair of cells 6, the first set of sensor elements from one cell 6a, for example Cell 1, is positioned adjacent the first set of sensor elements from the second cell 6c, Cell 2. The second set of sensor elements 6b from Cell 1 then is placed next adjacent the first set of sensor elements 6c from Cell 2; the second set of sensor elements 6d from Cell 2 then follows adjacent the second set of sensor elements 6b from the first cell, Cell 1. This arrangement is repeated for each of the other pairs of sensor cells 6. As discussed above, all the sensor elements, all the sensor cells and consequently all the pairs of sensor cells 6 are located side-by-side with each other along the length of the mounting frame 4.

The matching of sensor elements 6-1 to 6-6 in each sensor cell makes each cell 6 insensitive to overall changes in light, i.e. a change in light over the entire width of the carpet 3. Nonetheless, the matching of the sensor elements 6-1 to 6-6 and the pairing of sensor cells 6 allow the sensor elements to be sensitive to local defects in the carpet 3. Further, the matching of the sensor elements 6-1 to 6-6 makes them inherently adaptable to different carpet styles, patterns and densities.

Figure 7:
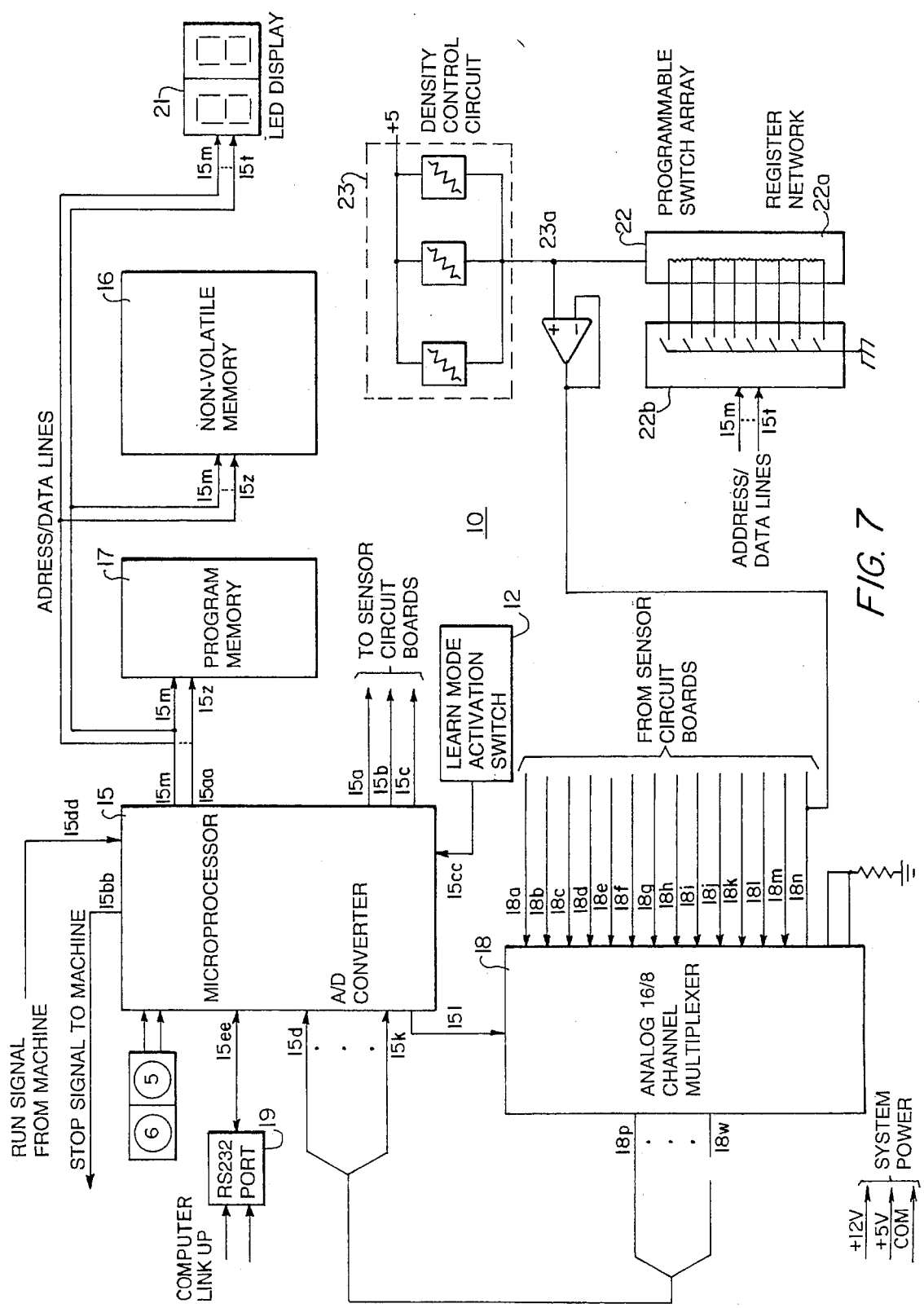
FIG. 7 illustrates a circuit block diagram of the control circuit 10 of the apparatus of the invention.

As illustrated in FIG. 7, the control circuit 10 incorporates a microprocessor 15, non-volatile memory 16, program memory 17, an analog 16-to-8 channel multiplexer circuit 18, an RS-232 port 19, a system sensitivity control switch device 20, a display 21, a programmable switch array for controlling the calibration of the density sensor cells 21, a LEARN mode activation switch 12, and a density sensor circuit 24.

The microprocessor 15, non-volatile memory 16 and program memory 17 may be of any conventional type capable of handling the operation of the apparatus as will be described below. In this first embodiment, the microprocessor 15 is a Motorola MC68HC11A1FN microprocessor that includes an A/D converter. Other types of microprocessors having A/D converters or microprocessors with a separate A/D converter circuit device included may be substituted.

The non-volatile memory 16 is used for the storage of data specific to the carpet currently being produced or intended to be produced. Such data may include parameters for the system's different applications (i.e., different types of machines, different types of carpet, or different carpet patterns). In this first embodiment, the parameters are stored in the non-volatile memory in the form of maximum and minimum signal and set point values determined during the LEARN mode operation, as will be explained below. In order to prevent the loss of such data whenever the machine is shut down or when a power outage occurs, non-volatile memory 16 such as a Dallas Semiconductor DS1230AB RAM is used. This particular type of RAM includes a battery to maintain the contents of its memory locations when no power is applied to the system.

The program memory 17 is used for storing the program code that operates the apparatus. In this embodiment, a Texas Instrument 27C256 EPROM is used.

The analog 16-to-8 channel multiplexer circuit 18 is connected at its input terminals to the output terminals 14i of each of the sensor circuit boards 7 (13 sensor boards with output terminals connected to input terminals 18a–18m in this first embodiment). The multiplexer circuit 18 multiplexes up to 16 analog signals from each of the sensor circuit boards 7 into eight analog signals from its output terminals 18p–18w to the A/D converter input terminals 15d–15k of the microprocessor 15. The multiplexer circuit 18 is also connected to receive the output signals from the density sensor cell 13 on a selected sensor circuit board 7 at the input terminal 18n. When more than one sensor circuit board 7 is equipped with a density sensor cell 13, the outputs of all the density sensor cells 13 are connected in parallel to each other as a density sensor 23 circuit, and then into the input terminal 18n of the multiplexer circuit 18 as shown in FIG. 7.

Figure 8:
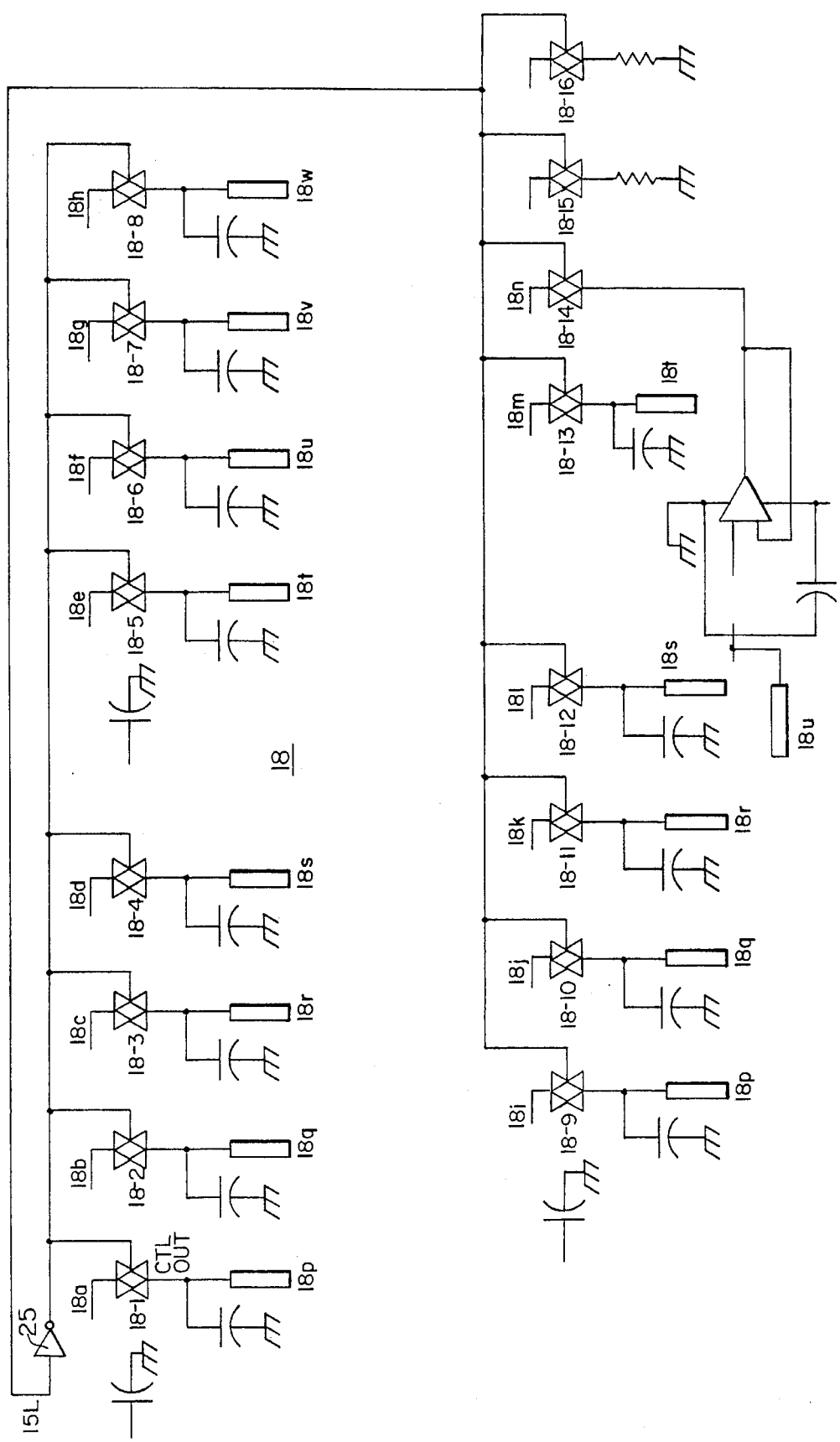
FIG. 8 illustrates a circuit diagram of one example for the 16-to-8 channel multiplexer circuit in the control circuit 10 of the invention.

The analog 16-to-8 channel multiplexer circuit 18 used in the first embodiment consists of a plurality of Motorola 74HC4066 bilateral switches 18-1 through 18-16 (in this case, up to sixteen switches) each connected between the output terminal 14i of a sensor circuit board 7 and an input terminal 15d–15k of the microprocessor's A/D converter 15 as shown in FIG. 8. In this embodiment, the bilateral switches are separated into two groups, the first group consisting of switches 18-1 through 18-8 and the second group consisting of switches 18-9 through 18-16. The input terminal IN of each switch is connected to an input terminal 18a–18n of the multiplexer circuit 18, and the output terminal OUT of each switch is connected to the output terminals 18p–18w. The control terminals CTL of the first group of switches 18-1 through 18-8 are connected in parallel to an ENABLE signal from the output terminal 15l of the microprocessor 15. Similarly, the control terminals CTL of the second group of switches 18-9 through 18-16 are connected in parallel to the ENABLE signal from the output terminal 15l, except through an inverter circuit 24. The ENABLE signal from the output terminal 15l is used to control switching between the two groups into which the sensor circuit boards 7 are divided. The above-described connection of the control terminals CTL to the output terminal 15l results in the first group always receiving an ENABLE signal opposite that received by the second group. This effectively implements the 16-to-8 multiplexing by alternately activating/deactivating each group of switches. The activated switches are able to pass the analog signals from their corresponding sensor circuit boards 7, while the deactivated switches are cut off.

In this first embodiment, thirteen sensor circuit boards 7 and the density sensor circuit 23 are connected to the control circuit 10. The microprocessor 15 receives signal from the first eight sensor circuit boards 7 as the first group using switches 18-1 through 18-8, and the remaining five sensor circuit boards 7 and density sensor circuit as the second group using switches 18-9 through 18-14.

The microprocessor 15 further provides select signals to each of the sensor circuit boards 7 which it uses in conjunction with the ENABLE signal 15l to select which sensor cell 6 from all the sensor circuit boards 7 to interrogate. As shown in FIG. 7, the select signals are embodied in three select signal output terminals 15a–15c from the microprocessor 15; the sensor circuit boards 7 are each connected to receive the three select signals outputted from terminals 15a–15c. For any given select signal outputted form terminals 15a–15c, each of the sensor circuit boards would transmit a signal based on the signal outputted from the output terminal from the sensor cell 6 identified by a given select signal. For example, with a select signal combination of 000, each of the sensor circuit boards 7 would output a signal representing the output of Cell 1 from its C1OUT terminal. With a select signal combination of 001, each of the sensor circuit boards 7 would output a signal representing the output of Cell 2 from its C2OUT terminal. In essence, all of a particular type of sensor cell 6 (i.e., Cell 1, Cell 2) are interrogated in parallel by the microprocessor 15.

The RS-232 port 19 to the I/O terminal 15ee of the microprocessor 15 is used to provide communication with a remote computer or terminal. This allows the signals and set points of each of the sensor cells to be remotely monitored in real-time operation. Overall, the RS-232 port access to the microprocessor 15 provides a user the ability to conduct detailed analyses or troubleshooting of the apparatus.

The system sensitivity control switch device 20 is used to control the relative sensitivity of the control circuit 10 to the range of signals that it may receive from the sensor cells 6. This will be explained further in connection with the operation of the system's software. In this first embodiment, the device 20 is implemented using two thumb wheel switches made by Cherry for setting the desired sensitivity level, and a Motorola 74HC541 octal buffer.

The display 21 is used to show system status and which sensors have detected a defect. The display 21 is embodied in a conventional two-digit LED display.

The programmable switch array 22 for controlling the calibration of the density sensor cells 13 uses a resistor network 22a and a switching circuit 22b to set the density cell signal level. Control signals from the output terminals 15m–15t of the microprocessor 15 are used to selectively set the resistors in the network 22a to ground using the switching circuit 22b. The purpose of selectively setting the resistors to ground is to implement a voltage divider between the resistor network 22a and the density sensor circuit 23. As shown in FIG. 7, the density sensor circuit 23 and the resistor network 22a are connected in series to GND. The voltage division is in turn intended to set the voltage level of the density signal at 23a inputted to the multiplexer circuit 18 at one-half the power supply voltage (2.5 volts). In this embodiment, the switching circuit 22b is implemented using a Motorola 74HC573 octal latch and a Motorola 74HC4051 8-channel multiplexer/demultiplexer to input the control signals 15m–15t from the microprocessor 15 to the resistor network 22a.

The LEARN mode activation switch 12 is connected to the input terminal 15cc of the microprocessor 15. The activation switch 12 is used to initiate the process of the apparatus "learning" the pattern of the carpet 3 or other material to be scanned. This will be explained in more detail below. In this embodiment, the activation switch 12 is implemented using a conventional momentary contact switch.

In operation, the sensor cells 6 in the sensor assembly 1 are aimed at the high frequency fluorescent light 2 and are "looking through" a carpet 3 or other material passing in between the sensor cells 6 and the fluorescent lamp 2. The sensor cells 6 detect the amount of light that is able to pass through the carpet 3. As discussed above, the microprocessor 15 measures the carpet density at each sensor cell 6. In particular, the microprocessor interrogates each sensor cell 6 one after the other across the length of the sensor assembly 1 and the width of the carpet 3. In this first embodiment, the carpet density is effectively measured by eight sensor cells 6 grouped in four pairs on each of thirteen sensor circuit boards 7. Each pair of sensor cells 6 covers four inches of the carpet's width. With thirteen sensor circuit boards 7, each board having four pairs sensor cells 6 and each sensor cell 6 being four inches long, the sensor assembly 1 can effectively scan a carpet over seventeen feet wide (17.333 feet wide). A carpet between 12–16 feet wide may be scanned once in approximately 28 msec or less by the interrogation of the microprocessor 15. This allows the microprocessor to scan the carpet 3 several times along any one width before the carpet 3 is indexed forward out of the machine.

A local change in carpet density will signal the existence of a defect in the carpet 3. That is local change in density is detectable by the sensor cell 6 as a change in the amount of light detected through the carpet 3. Specifically, the configuration of the sensor elements 6-1 to 6-6 in a sensor cell 6 as two matched sets 6a, 6b and the application of the +5 volt power supply across all the sensor elements results in a balanced voltage output at the output terminal of the sensor cell 6 between the two matched sets 6a, 6b. In this embodiment, voltage division of the two matched sets 6a, 6b operating as two equal resistance loads results in an output voltage one-half the power supply voltage (i.e., +2.5 volts). A local change in the amount of light detected by any of the sensor elements 6-1 to 6-6 will cause an imbalance in the resistance loads of the two matched sets. Consequently, that imbalance results in a change in the voltage level of the signal normally outputted by the sensor cell 6. The change in voltage levels is proportional to the increased or decreased amount of light sensed by the sensor cell 6. The change in voltage levels may itself be an increase or a decrease.

The pairing of sensor cells 6-1 to 6-6 and their physical configuration as described above addresses the problem of a defect in the carpet 3 occurring where the sensor cells 6 may not be able to detect defects if the sensor cells 6 were not so paired. Specifically, if the sensor cells 6 were not paired or configured as described above, local defects that occur between the two sets 6a, 6b of sensor elements of a cell, or that are large enough to cover an entire cell may not be detected by the sensor cells 6. In the case of defects between the two sets of a cell, the size and/or location of those defects relative to the center of the sensor cell 6 may not be sufficient to create the imbalance needed to cause the voltage level change. With defects large enough to cover an entire cell, unless an adjacent cell was able to detect the defect, that defect would simply not cause an imbalance.

By pairing the sensor cells 6 and by configuring the cells as described above, defects occurring between any two adjacent sets of sensor elements are actually being scanned by two separate sensor cells 6. As a result, an imbalance in resistance loads may occur in one or both sensor cells 6, thereby detecting the defect.

The density sensor cells 13 in selected sensor circuit boards 7 are used to detect sudden density changes along the entire width of the carpet 3 or other material being scanned. Such sudden changes in density over the whole carpet are indicative of malfunctions in the machine making the carpet 3 or material being scanned. As described above, a scanner assembly 1 having a plurality of sensor circuit boards 7 will incorporate density sensors cells 13 located on at least some of the sensor circuit boards 7. In this first embodiment, three density sensor cells 13 are used as shown in FIG. 7. In the sensor assembly 1, these three density sensor cells 13 are located in the sensor circuit boards 7 at both ends and in the middle of the sensor assembly 1 (not shown).

In FIG. 7, the three density sensor cells 13 are connected in parallel to each other as a density sensor circuit 23, and then in series with the programmable switch array 22 of the control circuit 10 to ground GND. The connection between the density sensor circuit 22 and the programmable switch array 22 is then connected to the input terminal of the microprocessor's A/D converter. As described above, the programmable switch array 22 consists of a programmable resistor network 22a with a switching array 22b controlled by the microprocessor 15. Through the switching array 22b, the microprocessor 15 sets the network 22a with a total resistance value that balances with the resistance of the density sensor circuit 23. Consequently, through voltage division, the input node 23a between the density sensor circuit 23 and the resistor array 22a of the programmable switch array 22 has an initial net voltage level at the input terminal 18n of the multiplexer circuit 18 that is one-half the power supply voltage. Again, in this case, that voltage is set to +2.5 volts.

A change in the density of the carpet 3 across its width sufficient to cause a noticeable change in the total resistance of the density sensor circuit 23 will cause an imbalance with the resistance set in the resistor network 22a of the programmable switch array 22. The resulting change in the voltage level inputted into the A/D converter of the microprocessor 15 is interpreted by the microprocessor 15 to mean a malfunction with the machine producing the carpet 3. When the microprocessor 15 detects such a malfunction, it may then warn an operator and/or stop the operation of the machine. In this embodiment, the microprocessor 15 outputs a STOP signal from its output terminal 15bb to the machine. When the machine is first activated or put back into operation by an operator, the machine may also send a RUN signal to the microprocessor 15 through the input terminal 15dd signalling the control circuit 10 to resume its control operation.

Before beginning full operation of the scanning system, an operator would first determine whether the carpet 3 to be produced is the same as that last produced on the machine or a different type. If the same, the non-volatile memory 16 of the control circuit 10 would already contain all the parameters for the carpet 3, and the system sensitivity control switch device 20 would have the proper sensitivity level already set. If the carpet 3 to be produced is different, then the operator would initiate the LEARN mode by activating the LEARN mode input device 23. The LEARN mode input device 23 is activated using the LEARN mode activation switch 12. In this embodiment, the activation switch 12 through the input device 23 sends a command signal to the microprocessor 15 to run the program code that controls the LEARN mode.

In the LEARN mode, an example of the type of carpet 3 to be scanned is passed under the sensor assembly 1. The microprocessor 15 monitors the signals generated by the sensor cells 6 to determine a statistical range of signal voltage levels that the microprocessor 15 will encounter while scanning the carpet 3. The range of signal voltage levels for any one type of carpet will vary based on the carpet's density, pattern, and color (in terms of gray-scale). As the system is scanning the carpet 3, the control circuit 10 is storing the values of the signal voltage levels and comparing those values with each other. From that comparison, the microprocessor 15 statistically determines a range of signal voltage levels that it will recognize as being normal for that particular type of carpet. In particular, the microprocessor 15 determines maximum and minimum values for the signal voltage levels. Using the setting of the system sensitivity control switch device, the microprocessor 15 calculates modified maximum and minimum range limits that are either equal to or broader than the original statistically-determined range limits. In other words, the modified maximum and minimum limits either widen or narrow the range limits from the original statistically-determined range limits. By doing so, a user may control the degree to which the control circuit 10 is sensitive to detecting the statistically-determined maximum and minimum range limits.

For example, wider maximum and minimum range limits will result in a less sensitive detection of defects, while narrower maximum and minimum range limits will result in a more sensitive detection of defects. Wider range limits and less sensitivity are desirable when scanning carpets that have wide variations in density, pattern and color. Such wide variations create considerable degrees of noise in the output signals of the sensor cells 6. Otherwise, greater levels of sensitivity would cause the machine to stop constantly and unnecessarily.

Narrower range limits and more sensitivity are desirable when scanning carpets that have few or no variations in density, pattern or color. For example, plain one-color carpets create little noise in the output signals from the sensor cells 6. In this case, since the characteristics of the carpet are supposed to be more uniform, any detectable deviations from the statistically-determined range limits are more likely to be defects.

The actual degree to which the range limits are widened or narrowed are set by an operator on the system sensitivity control switch device 20. The value set in the switch device 20, in this case through thumbwheel switches, is selected based on the type of carpet being scanned. An operator may input values into the device using values from a prior production of the same carpet now being produced, or through trial and error, and experimentation to determine an optimum setting for the switch device 20. In this first embodiment, the numerical setting range on the thumbwheel switches is 0–99 which is then inversely translated into a range of 30% to 0% wider than the statistically-determined range limits. For example, a setting of 0 translates to a range of 30% above the maximum value limit and 30% below the minimum value limit. A setting of 99 translates into a range having the statistically-determined maximum and minimum value limits.

In a typical application of the invention, the apparatus is positioned in a machine that manufactures the carpet immediately following the mechanism that stitches the yarn onto the carpet. In general, as one linewidth area or stitch of the carpet is being done, the linewidth area or stitch that was just previously done is being scanned.

Figures 9, 10:
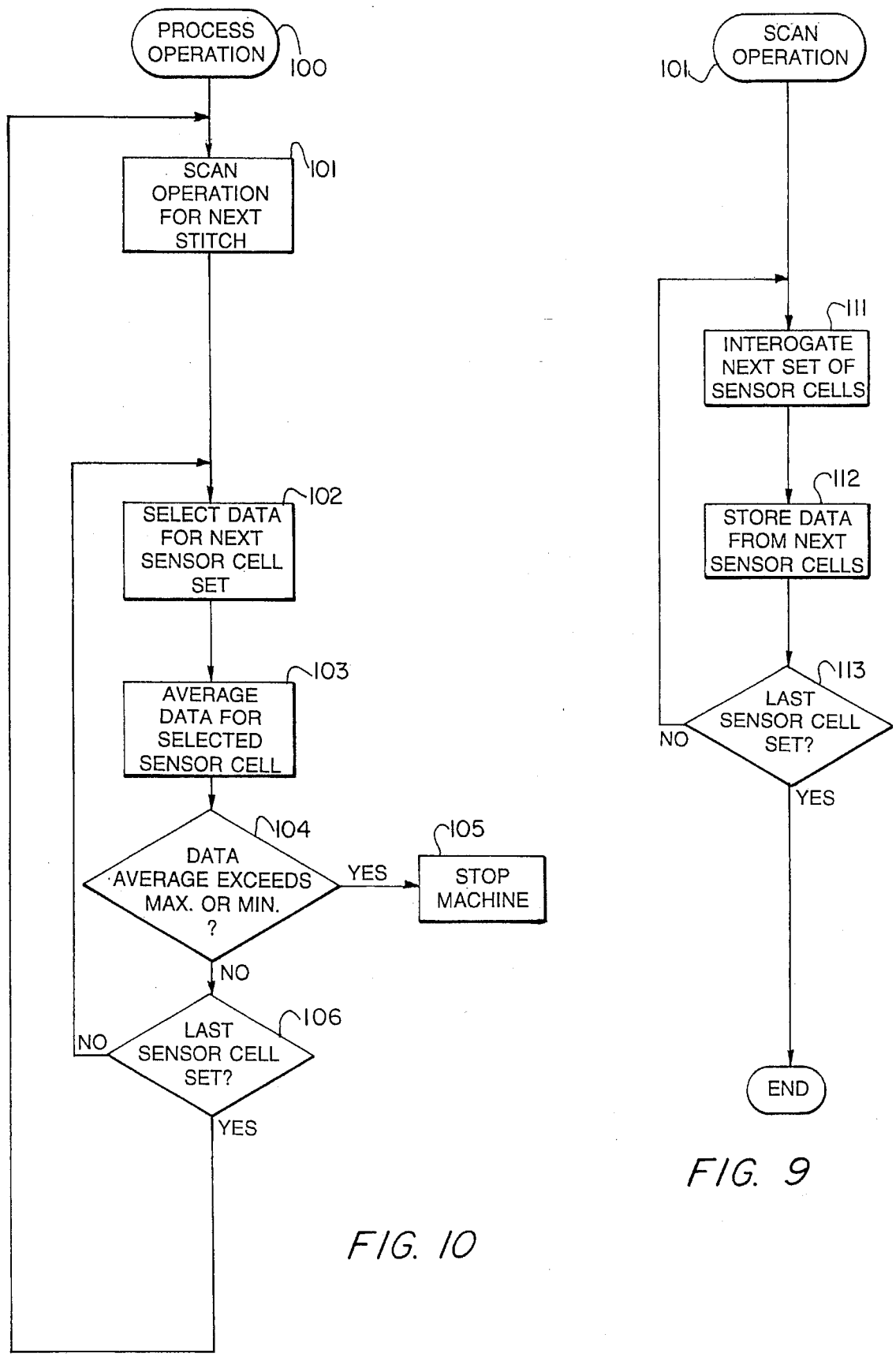
FIG. 9 illustrates a flow chart of the PROCESS mode operation of the present invention.
FIG. 10 illustrates a flow chart of the SCAN subroutine operation of the present invention.
Figure 11:
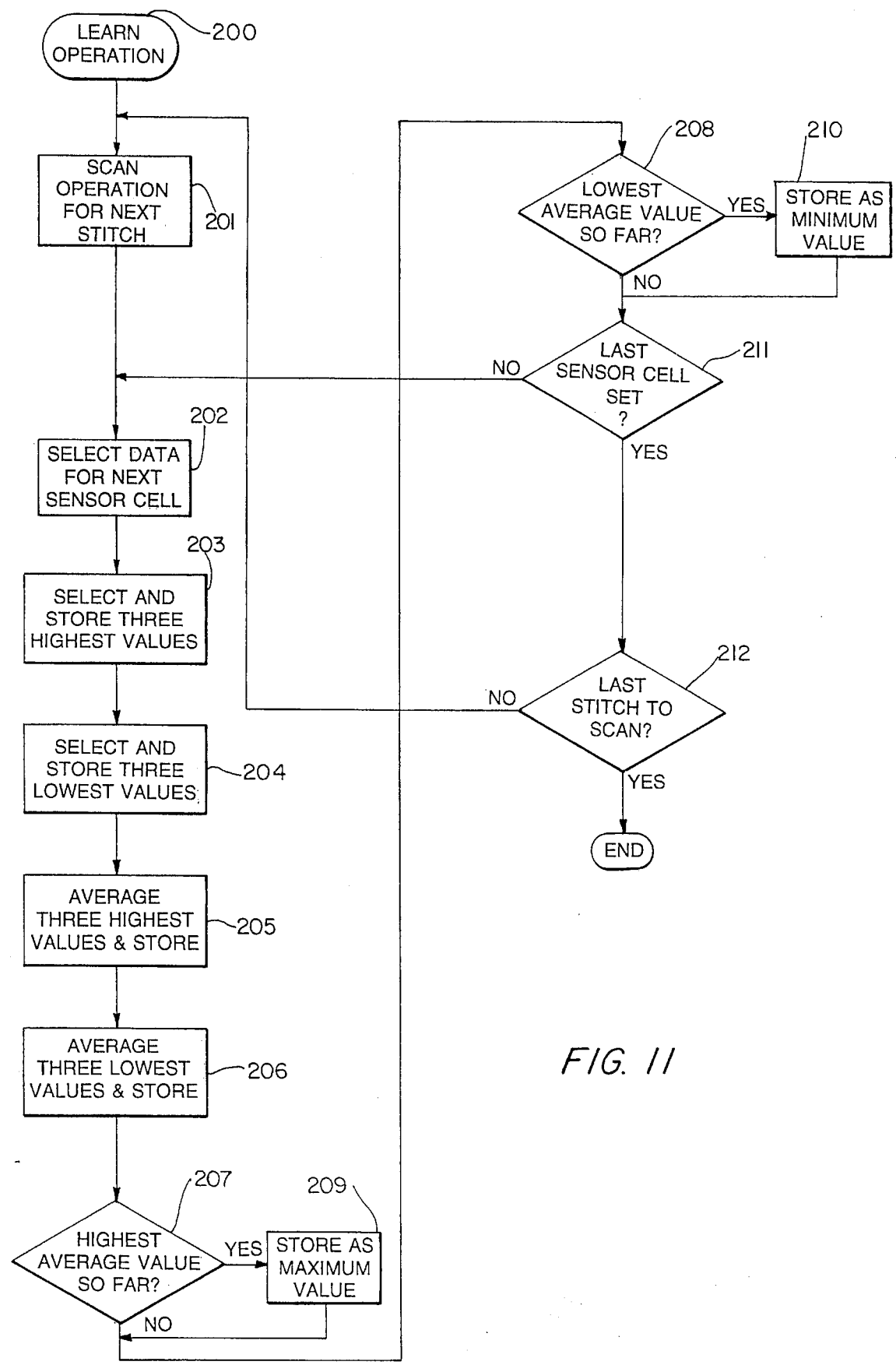
FIG. 11 illustrates a flow chart of the LEARN mode operation of the present invention.

In the operation of the software as illustrated in FIGS. 9–11, the operation generally consists of a SCAN subroutine operation 101 (FIG. 9), a PROCESS mode operation 100 (FIG. 10), and a LEARN mode operation 200 (FIG. 11). The SCAN mode operation 101 is implemented in the PROCESS mode operation 100 as Step 101, and in the LEARN mode operation 200 as Step 201.

In FIG. 9, the SCAN subroutine operation 101 may generally comprise the steps of selecting a specific sensor cell in each of the sensor circuit boards and interrogating that set of selected sensor cells (Step 111) and storing data values from that set of selected sensor cells (Step 112). If that set of selected sensor cells is the last set of sensor cells on the each of the sensor circuit boards, the SCAN subroutine ends and proceeds with other operations within the PROCESS mode operation. If that set of selected sensor cells is not, the next set of sensor cells is selected (Steps 113, 111). The number of times one linewidth or stitch of the carpet is scanned is determined by the type of carpet being produced. The more time the machine requires to make the next stitch of carpet, the more time the system has to scan the previously made stitch. Consequently, the more times a stitch is scanned, the more data the system generates and stores for that one stitch.

As shown in FIG. 10, the PROCESS mode operation (Step 100) for the normal scanning of a carpet may generally include the steps of the SCAN subroutine (Step 101), selecting the stored data for one set of sensor cells for the stitch that was scanned, and selecting and examining the data for that one selected set of sensor cells (Step 102). The data values for the selected set of sensor cells are averaged together (Step 103), and then compared with the statistically-determined maximum and minimum values discussed above (Step 104). If the averaged value for the selected set of sensor cells is either more than the maximum value or less than the minimum value, then the system stops the machine (Step 105). If the selected set of sensor cells is the last set of sensor cells on all the sensor circuit boards, the PROCESS mode operation conducts the same steps for the next stitch generated (Steps 106, 101). If the selected set of sensor cells is not, the next set of sensor cells is selected (Steps 106, 102). At this point, the machine indexes the carpet allowing the system to scan that next stitch, while the machine begins generating a new stitch.

As discussed above, the LEARN mode operation is initiated when the LEARN mode activation switch 12 is used. As shown in FIG. 11, the LEARN mode operation (Step 200) first includes the step of the SCAN subroutine (Step 201) which is the same subroutine used by the PROCESS mode operation. The LEARN mode operation then selects the stored data for one set of sensor cells for the stitch that was scanned (Step 202). Based on the number of times one stitch may have been scanned as discussed above, the three highest data values for the selected set of sensor cells are selected (Step 203), and the three lowest data values for the selected set of sensor cells are selected (Step 204). The three highest values are then averaged (Step 205), while the three lowest values are then averaged (Step 206). At Steps 207 and 208, these calculated averaged values for the selected set of sensor cells are compared with any previously stored values for that set of sensor cells to determine if they are the highest and lowest average values. If so, the values are stored accordingly as the new maximum and minimum values of the signal level range for that set of sensor cells (Steps 209, 210). If the selected set of sensor cells is the last set on all the sensor circuit boards, the LEARN mode operation conducts the same steps for the next stitch generated (Steps 211, 212, 201). If the selected set of sensor cells is not, the next set of sensor cells is selected (Steps 211, 202). If the selected set of sensor cells is the last set, as with the PROCESS mode operation, the machine indexes the carpet allowing the system to scan that next stitch, while the machine begins generating a new stitch.

When the data values for the selected sensor cell are compared with any prior maximum and minimum values then stored as the new maximum and/or minimum values (Steps 207–210), the system also re-calculates those values based on the setting or set points of the system sensitivity control switch device 20. In other words, based on the set point value from the system sensitivity control switch device 20, the maximum and/or minimum values to be stored are recalculated as 0 to 30% above or below, respectively, their original values.

The SCAN subroutine (Step 201) is performed for a predetermined number of stitches of the carpet 3 in order to scan the entire pattern of the carpet to be "learned." In this first embodiment, the SCAN subroutine (Step 201) is performed in the LEARN mode operation for a thousand stitches. When the predetermined number of stitches are scanned, the system reverts back to its PROCESS mode operation depending on when an operator activates the system. The data obtained from the LEARN mode operation is stored in the non-volatile memory 16.

Modifications and variations of the above-described embodiments of the present invention are possible, as appreciated by those skilled in the art in light of the above teachings. For example, the mounting frame 4 and/or the protective cover 5 may be fabricated from different materials or in several components. Instead of an optically diffusive material, the protective cover 5 may be made from an optically transparent material with a diffuser layer added. Instead of light sensitive resistors, phototransistors or photodiodes may be used to achieve faster response times provided the needed changes are made to the operating software of the apparatus are made to accommodate the spectral response characteristics of either device. Also, different shapes of light sensitive resistors may be used.

Further, the present invention as disclosed above may have other applications that would be appreciated by those skilled in the art in light of the above teachings. Such applications include but are limited to the use of the apparatus with weaving machines, knitting machines, final inspection of knitted or woven products, and the inspection of paper products. The present invention as disclosed may be applied to virtually to any process for the manufacture and/or inspection of translucent materials.

It is therefore to be understood that, within the scope of the appended claims and their equivalents, the invention may be practiced otherwise than as specifically described.

What is claimed is:

1. A system for scanning a carpet for tuft defects, said system comprising:

a light source for providing light along a width of said carpet;

a scanning array for detecting light from said light source passing through said carpet, said scanning array having at least one pair of first and second sensor cells, and being positioned opposite said light source with said carpet passing transversely therebetween, wherein each of said first and second sensor cells includes first and second sets of sensor elements, each of said first and second sensor cells having an output node between said first and second sets of sensor elements, said output node outputting a signal detecting tuft defects in said carpet based on an amount of light passing through said carpet, said first set of sensor elements of said second sensor cell being positioned adjacent said first set of said first sensor cell, said second set of said first sensor cell being positioned adjacent said first set of said second sensor cell, and said second set of said second sensor cell being positioned adjacent said second set of said first sensor cell, and said first and second sensor cells are positioned longitudinally in said sensor array; and control circuit means for controlling said sensor array to scan said carpet and for receiving said output signals from said first and second sensor cells detecting tuft defects in said carpet based on said light passing through said carpet.

2. A system for scanning a carpet for tuft defects during manufacture, said system operating in connection with a machine manufacturing said carpet, said system comprising:

a light source for providing light along a width of said carpet being manufactured;

a scanning array for detecting tuft defects in said carpet being manufactured, said scanning array having at least one pair of first and second sensor cells, and being positioned opposite and parallel said light source with said carpet passing transversely therebetween, wherein said first and second sensor cells are positioned longitudinally in said sensor array and parallel to said light source, each of said first and second sensor cells includes first and second sets of sensor elements, said first set having a first number of sensor elements and said second set having a second number of sensor elements, each of said first and second sensor cells having an output node between said first and second sets of sensor elements, said output node outputting an output signal indicating an electrical balance between said first set and said second set of sensor elements based on an amount of light from said light source passing through said carpet, and said first set of sensor elements of said second sensor cell being positioned adjacent said first set of said first sensor cell, said second set of said first sensor cell being positioned adjacent said first set of said second sensor cell, and said second set of said second sensor cell being positioned adjacent said second set of said first sensor cell; and control circuit means for controlling said sensor array to scan said carpet and for determining detection of tuft defects in said carpet based on said output signal from each of said first and second sensor cells.

3. A system as claimed in claim 2, wherein said first number of sensor elements in said first set is electrically equal to said second number of sensor elements in said second set.

4. A system as claimed in claim 2, wherein said sensor elements include light sensitive resistors.

5. A system as claimed in claim 2, wherein said light source is a high-frequency fluorescent lamp.

6. A system for automatically scanning a carpet for tuft defects, said system being connected to operate in coordination with a conveying operation of said carpet, said system comprising:

a light source for providing light along a width of said carpet;

a scanning array for detecting tuft defects in said carpet, said scanning array having a plurality of pairs of first and second sensor cells, said scanning array positioned opposite and parallel to said light source with said carpet passing transversely therebetween, said plurality of first and second sensor cell pairs being positioned adjacent and longitudinally with each other along said scanning array to detect light from said light source passing through said carpet, wherein each of said first and second sensor cells includes a first and second set of sensor elements with an output node electrically connected therebetween, said first set having sensor elements forming a resistance load proportional to a resistance load formed by sensor elements in said second set based on an amount of said light passing through said carpet, and said first set of sensor elements from said second sensor cell being positioned adjacent said first set from said first sensor cell, said second set from said first sensor cell being positioned adjacent said first set from said second sensor cell, and said second set from said second sensor cell being positioned adjacent said second set from said first sensor cell; and control circuit means for controlling said sensor array to scan said carpet and for determining detection of tuft defects in said carpet, said control circuit means including means for receiving an output signal from said output node of each of said first and second sensor cells, said output signal indicating detection of tuft defects based on a proportional imbalance between said resistance loads of said first and second sets of sensor elements.

7. A system as claimed in claim 6, wherein said sensor elements are light sensitive resistors, and each said first set of sensor elements forms a resistance load proportionally equal to a number of light sensitive resistors in said second set of sensor elements.

8. A system as claimed in claim 7, wherein a number of said light sensitive resistors in said first set of sensor elements is equal to a number of light sensitive resistors in said second set of sensors.

9. A system as claimed in claim 6, wherein said sensor array further includes a plurality of sensor circuit boards,
  each of said sensor boards having mounted thereon a subset of said plurality of pairs of first and second sensor cells, and a multiplexer device for multiplexing output signals from said output nodes of said first and second sensor cells and for outputting a multiplexed output data signal to said control circuit means.

10. A system as claimed in claim 9, wherein said control circuit means includes a multiplexer circuit for multiplexing said multiplexed output data signals outputted from each of said plurality of sensor boards connected to said control circuit means.

11. A system as claimed in claim 6, further comprising at least one density sensor cell for detecting wide scale defects in said carpet, said wide scale defects being indicative of malfunctions in said machine manufacturing said carpet.

12. A system as claimed in claim 10, wherein selected ones of said sensor circuit boards include a density sensor cell for detecting wide scale defects in said carpet, said wide scale defects being indicative of malfunctions in said machine manufacturing said carpet.

13. A system as claimed in claim 12, wherein density sensor cells on said selected ones of said sensor circuit boards are connected in parallel to each forming a density sensor circuit, said density sensor circuit outputting a density sensor signal to said control circuit means as an input to said multiplexer circuit of said control circuit means.

14. A method for scanning a carpet for tuft defects, said method being implemented in a sensor array operating in connection with a conveying operation of said carpet, said method comprising the steps of:
  providing said scanning array opposite and parallel a light source with said carpet passing transversely therebetween;
  providing said scanning array with a plurality of pairs of first and second sensor cells for detecting light passing through said carpet, said plurality of first and second sensor cell pairs being positioned adjacent each other longitudinally in said scanning array, wherein
  each of said first and second sensor cells are provided with a first and second set of sensor elements, and each of said first and second sensor cells outputs an output signal indicating an electrical balance between said first and second sets of sensor cells;
  further providing said first set of sensor elements from said second sensor cell to be positioned adjacent said first set from said first sensor cell, said second set from said first sensor cell positioned adjacent said first set from said second sensor cell, and said second set from said second sensor cell positioned adjacent said second set from said first sensor cell;
  scanning a stitch of said carpet along an entire width of said carpet with said scanning array;
  detecting output signals from each of said plurality of first and second sensor cells based on an amount of light detected by each of said plurality of first and second sensor cells; and
  determining whether said output signals indicate detection of tuft defects in said carpet based on said amount of light detected by said plurality of first and second sensor cells.

15. A method as claimed in claim 14, wherein said step of determining whether said output signals indicate detection of tuft defects in said carpet is further based on an electrical imbalance between said first and second sensor cells resulting from said amount of light passing through said carpet and detected by said plurality of first and second sensor cells.

16. A method for scanning a carpet for tuft defects, said method being implemented in a sensor array operating in connection with manufacture of said carpet, said method comprising the steps of:
  providing said scanning array opposite and parallel a light source with said carpet passing transversely therebetween to detect tuft defects in said carpet;
  providing said scanning array with a plurality of pairs of first and second sensor cells, said plurality of first and second sensor cell pairs being positioned adjacent and longitudinally with each other along said scanning array, wherein
  each of said first and second sensor cells are provided with first and second sets of sensor elements and an output node therebetween, said first set having sensor elements that form a resistance load proportional to a resistance load formed by sensor elements in said second set;
  further providing said first set of sensor elements from said second sensor cell to be positioned adjacent said first set from said first sensor cell, said second set from said first sensor cell positioned adjacent said first set from said second sensor cell, and said second set from said second sensor cell positioned adjacent said second set from said first sensor cell;
  scanning a stitch of said carpet along an entire width of said carpet with said scanning array;
  detecting data signals at said output node of each of said plurality of first and second sensor cells based on an amount of light detected passing through said carpet;
  comparing said signal values of said data signals with predetermined maximum and minimum signal values to determine whether said signal values are at least one of greater than said predetermined maximum value and less than said predetermined minimum value; and
  determining whether tuft defects have been detected in said carpet based on said comparing of said signal values.

17. A method as claimed in claim 16, further comprising the step of:
  controlling manufacturing of said carpet based on a result of said determination including stopping said manufacturing when a tuft defect is detected, said tuft defect being detected when at least one of said signal values is greater than said predetermined maximum value or less than said predetermined minimum value.

18. A method as claimed in claim 16, wherein said step of scanning a stitch of said carpet along an entire width of said carpet includes the steps of accessing each of said first and second sensor cells progressively along a length of said sensor array, in order to receive a data signal from said output node of each of said first and second sensor cells.

19. A method as claimed in claim 18, wherein said step of scanning a stitch of said carpet along an entire width of said carpet is repeated a number of times in accordance with a type of carpet being scanned.

20. A method as claimed in claim 16, wherein said step of providing said sensor array includes providing said sensor array with a plurality of sensor circuit boards having mounted thereon a subset of said plurality of pairs of first and second sensor cells, and
  said step of scanning a stitch of said carpet along an entire width of said carpet includes the steps of accessing each of said sensor circuit boards along a length of said sensor array, and within each sensor circuit board accessing each of said first and second sensor cells to receive a data signal from said output node of each of said first and second sensor cells.

21. A method as claimed in claim 20, wherein said step of scanning a stitch of said carpet along an entire width of said carpet is repeated a number of times in accordance with a type of carpet being scanned.

22. A method as claimed in claim 16, further comprising the step of:

providing at least one density sensor cell among said first and second sensor cells for detecting wide scale defects in said carpet, said wide scale defects being indicative of malfunctions in said machine manufacturing said carpet, wherein said step of scanning a stitch of said carpet includes accessing said at least one density sensor cell in order to generate a density data signal therefrom.

* * * * *